United States Patent [19]

Yamashita et al.

[11] Patent Number: 5,322,928

[45] Date of Patent: Jun. 21, 1994

[54] DIAPAUSE HORMONE ISOLATED FROM SILKWORM EXHIBITING IMPROVED DIAPAUSE ACTIVITY

[75] Inventors: Okitsugu Yamashita, Nagoya; Kunio Imai, Tsu; Minoru Isobe, Nagoya, all of Japan

[73] Assignee: Shionogi Seiyaku Kabushiki Kaisha, Osaka, Japan

[21] Appl. No.: 845,193

[22] Filed: Mar. 3, 1992

[30] Foreign Application Priority Data

Mar. 4, 1991 [JP] Japan .................................. 3-064022
Mar. 15, 1991 [JP] Japan .................................. 3-077043

[51] Int. Cl.$^5$ ...................... A61K 37/00; A61K 37/02; C07K 5/00; C07K 7/00
[52] U.S. Cl. .................................... 530/325; 530/300
[58] Field of Search .................... 514/12, 13; 530/300, 530/324, 325

[56] References Cited

PUBLICATIONS

Kubota et al, Agric. Biol. Chem, vol. 43(5), pp. 1075–1078, 1979.
Agricultural and Biological Chemistry, vol. 40, No. 6, Jun. 1, 1976, pp. 1189–1199, M. Isobe, et al., "Diapause Hormone B: Its Selective Extraction and Isolation From the Silkworm, *Bombyx mori*".
Chemical Abstracts, vol. 79, No. 7, Aug. 20, 1973, No. 39465m, M. Isobe, et al., "Chemistry Of The Silkworm Diapause Hormone. I. Isolation Of The Diapause Hormone From The Silkworm, *Bombyx mori*".
Biological Abstracts, vol. 62, No. 10, Oct. 1, 1976, No. 37482, I. Kubota, et al., "Molecular Size Of The Diapause Hormone Of The Silkworm *Bombyx mori*".
Proceedings of the Japan Academy, Series B, vol. 67, No. 6, 1991, pp. 98–101, K. Imai, et al., "Isolation and Structure of Diapause Hormone Of The Silkworm, *Bombyx mori*".

*Primary Examiner*—Lester L. Lee
*Assistant Examiner*—A. M. Davenport
*Attorney, Agent, or Firm*—Oblon, Spivak, McClelland, Maier & Neustadt

[57] ABSTRACT

This invention relates to a diapause hormone, a novel polypeptide, comprising 24 amino acids residues designated by the following amino acid sequence:

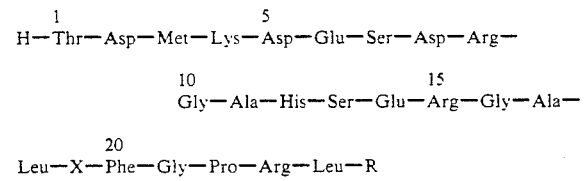

wherein X is Cys (SEQ ID NO:1) or Trp (SEQ ID NO:2) and R is OH or NH$_2$.

10 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 24 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( A ) ORGANISM: Bombyx mori
( D ) DEVELOPMENTAL STAGE: pupa
( F ) TISSUE TYPE: subesophagus, thoracic cavity
( G ) CELL TYPE: ganglion ( x i ) SEQUENCE DESCRIPTION: SEQ ID NO:1:

```
Thr Asp Met Lys Asp Glu Ser Asp Arg Gly Ala His Ser Glu Arg Gly
1               5                   10                  15

Ala Leu Cys Phe Gly Pro Arg Leu
            20
```

( 2 ) INFORMATION FOR SEQ ID NO:2:

( i ) SEQUENCE CHARACTERISTICS:
( A ) LENGTH: 24 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( A ) ORGANISM: Bombyx mori
( D ) DEVELOPMENTAL STAGE: pupa
( F ) TISSUE TYPE: subesophagus, thoracic cavity
( G ) CELL TYPE: ganglion ( x i ) SEQUENCE DESCRIPTION: SEQ ID NO:2:

```
Thr Asp Met Lys Asp Glu Ser Asp Arg Gly Ala His Ser Glu Arg Gly
1               5                   10                  15

Ala Leu Trp Phe Gly Pro Arg Leu
            20
```

DIAPAUSE HORMONE ISOLATED FROM SILKWORM EXHIBITING IMPROVED DIAPAUSE ACTIVITY

BACKGROUND OF THE INVENTION

1. Field of the Invention

The present invention relates to a diapause hormone, novel polypeptide, derived from *Subaesophageal ganglia* of a silkworm (*Bombyx mori*) pupa and the first thoracic ganglia of a silkworm (*Bombyx mori*) pupa. This polypeptide has comprises 24 amino acid residues designated by the following amino acid sequence:

```
  1                                    5
H—Thr—Asp—Met—Lys—Asp—Glu—Ser—Asp—Arg—
                 10                   15
                 Gly—Ala—His—Ser—Glu—Arg—Gly—Ala—
   20
Leu—X—Phe—Gly—Pro—Arg—Leu—R
``` wherein X is Cys (SEQ ID NO: 1) or Trp (SEQ ID NO: 2) and R is OH or $NH_2$.

2. Description of the Prior Art

Many species of insects diapause. There are two main hormonal mechanisms of the diapause; (1) lack of a hormone which stimulates the growth of insects, (2) secretion of a hormone which positively causes a diapause, that is, a diapause hormone. The structure of the diapause hormone has not yet been determined, but physiological properties of the hormone have been elucidated by using a partially purified diapause hormone. As one of the properties the hormone influences the formation of silkworm's eggs at a pupal stage. It acts on an ovary and specifically raises activity of trehalase locally existing in a cytolemma. Because a blood sugar of insects is trehalose, a rise of the trehalase activity contributes to an intake of a blood sugar into an ovary, resulting in accumulation and storage of carbohydrate, especially glycogen, in silkworm's eggs. In these nutritious eggs, sorbitol is synthesized from the glycogen at an embryo stage on the first day after a fertilization. The eggs enter diapause by the accumulation of sorbitol. That is to say, a large amount of sorbitol extremely decreases free water in a living body, and all reactions in the living body stop, whereby the living body is kept stable.

The structures of insect hormones, e.g., ecdysteroids, juvenile hormone, prothoracicotropic hormone, adipokinetic hormone, etc. have already been reported, wherein prothoracicotropic hormone and adipokinetic hormone are polypeptides.

The diapause hormone, secretory polypeptide, has not been isolated, purified, and sequenced prior to this invention.

SUMMARY

The present inventors first isolated and purified a secretory polypeptide in subaesophageal and first thoracic ganglia of a silkworm (*Bombyx mori*) pupa, found out that the polypeptide had diapause hormone activity, and determined the structure of the polypeptide. This invention relates to a polypeptide having diapause activity and comprising 24 amino acids residues designated by the following amino acid sequence:

```
  1                 5                    10                 15
H—Thr—Asp—Met—Lys—Asp—Glu—Ser—Asp—Arg—Gly—Ala—His—Ser—Glu—Arg—Gly—Ala—
     20
Leu—X—Phe—Gly—Pro—ArgLeu—R
``` wherein X is Cys (SEQ ID NO: 1) or Trp (SEQ ID NO: 2) and R is OH or $NH_2$.

DESCRIPTION OF THE PREFERRED EMBODIMENT

The polypeptide of this invention can be isolated and purified by conventional methods applied for peptides, e.g., extraction with solvents and low- or high-performance liquid chromatography.

The polypeptide of this invention can be synthesized by a solid phase peptide synthesizer.

A silkworm is an industrially valuable silk-producing insect. To efficiently produce eggs of silkworms and to preserve the eggs in safety are very important in the production of silk. The diapause hormone will positively be used for preservation and stable supply of the silkworm's eggs, because the eggs are diapaused and kept at an early stage by the hormone, which enables stable supply of silkworm's larvae.

In the meantime, some kinds of insects are harmful mainly at their growing stage on agriculture, forestry, and hygiene. The diapause hormone can positively diapause the harmful insects at the actively feeding stage and control them.

As described above, an elucidation of the diapause hormone has been desired for preservation and stable supply of the silkworm's eggs and control of the harmful insects.

EXAMPLE

1. Isolation and Purification

*Subaesophageal ganglia*, which are diapause hormone-secreting organs, were excised with the first *Thoracic ganglia* in insect physiological saline (0.75% NaCl) from about one hundred thousand silkworm (*Bombyx mori*) pupae immediately after the transformation to a pupa under an anatomy microscope to yield about 5 g of them. The obtained organs were put into 100% ethanol immediately after the excision, and then frozen and preserved at −20° C. The ganglions were recovered by low-speed centrifugation, and then triturated in 100% ethanol. The resultant was centrifuged at low speed to obtain a precipitate. The precipitate was washed with ethanol three times, and then extracted with 150 ml of methanol-dichloromethane (1:1) three times to obtain a precipitate. The obtained precipitate was washed with 150 ml of 50% 2-propanol three times and with 150 ml of 80% ethanol three times. To the resulting precipitate 150 ml of distilled water was added, heated in boiling water for 10 minutes, cooled on ice, and then centrifuged at 12,000 g for 20 minutes to obtain a supernatant. A remaining precipitate was extracted with water in the same manner as described above, and a resulting supernatant was added to the previously obtained supernatant. The extraction with hot water was effective for abolishing the activity of many proteases as well as for extracting the hormone.

The extract with hot water was evaporated to dryness under reduced pressure at 35° C. and dissolved in 1 ml of distilled water, and then insoluble material was filtered off with a filter paper whose pore size was 4.5 μm. The filtrate was applied on reversed phase high-performance liquid chromatography under the following condition.

HPLC apparatus: 880PU type high-performance liquid chromatograph (JASCO)

Column: TSKgel Octodecyl-4PW (4.6 mmID×150 mmL) (TOSOH Co.)

Condition of elution:
Solvent A: distilled and refined water
Solvent B: 2-propanol The column was equilibrated with solvent A for 30 minutes. On the column 200 μl of the above-obtained specimen was loaded five times, followed by washing the column with water for 15 minutes. Then, the column was put to gradient elution so that solvent B reached 7% in 10 minutes and 13% in 60 minutes to eliminate impurities.

Furthermore, the elution was carried out with 13% solvent B for 80 minutes. Then, it was continued so that solvent B reached 35% in 60 minutes, the status was remained for 30 minutes, and finally the column was washed with 100% solvent B to be regenerated.

Detector: 875 type UV absorption type detector (NIHON BUNKOHSYA). The detection was carried out at 210 and 280 nm.

The diapause hormone was eluted 100 to 120 minutes after the iniation of the gradient elution. The obtained hormone-activity was reseparated by reversed phase high-performance liquid chromatography conducted under the following condition.

HPLC apparatus and Column: the same as above
Condition of elution:
Solvent A; 0.05% trifluoroacetic acid
Solvent B; 2-propanol After the column was equilibrated with solvent A for 30 minutes, 200 μl of the specimen was loaded on the column five times, followed by washing the column with solvent A for 15 minutes. Then, the column was put to gradient elution so that solvent B reached 50% in 120 minutes. Finally, the column was washed with 100% solvent B to be regenerated.

A detector and condition of the detection were the same as above.

A bioassay was carried out on a lot of peaks of the chromatogram. As a result, only the sharp peak with retention time of about 50 minutes showed the hormonal activity and was identified as a diapause hormone. A yield of the hormone was about 1 μg.

2. Establishment of Structure

Using 500 ng of the isolated diapause hormone, structure of the hormone was analyzed by an automatic gas phase peptide sequencer (Model 477A/120A protein/-peptide sequencer PHT analyzer; Applied BioSystems). As a result, the structure of the diapause hormone was determined as follows:

```
         1              5                 10                15
H—Thr—Asp—Met—Lys—Asp—Glu—Ser—Asp—Arg—Gly—Ala—His—Ser—Glu—Arg—Gly—Ala—

20
Leu—X—Phe—Gly—Pro—Arg—Leu—OH (or NH2)
``` wherein X is Cys (SEQ ID NO: 1) or Trp (SEQ ID NO: 2).

Furthermore, after the hormone was cleaved with endoprotease Glu-C (Protease V8: specific to the C terminus of Glu), the cleavage products were separated by a conventional method using HPLC, and each product was sequenced by an gas phase peptide sequencer. As a result, though a part of the amino acid sequence could not be identified because of a very small amount of the specimen, an amino acid sequence of the longest peptide among the cleavage products was identical with that from position 15 to 24 of the above-established amino acid sequence of the diapause hormone. This result made the above hormonal structure confirmative.

Molecular weight of the hormone which was calculated from this structure agreed with 2,500 of molecular weight deduced from a gel filtration analysis (column; TSKgel 2000SW, TOSOH Co., developing solvent; 0.05% trifluoroacetic acid).

The fact that the diapause hormone had retention time of about 50 minutes on reversed phase high-performance liquid chromatograph analysis (TSKgel Octadecyl-4PW column, TOSOH Co., 0.05% trifluoroacetic acid-2-propanol system gradient elution, the same condition as that of the above purification in second step.) showed character of the molecule of the present hormone.

3. Assay of Bioactivity

There exists a strain of a silkworm which does not diapause, called non-diapause strain, e.g., N4 line. The hormonal activity was confirmed by the following method: the specimen is injected into the 4 days-age pupa of non-diapause strain. After the pupa transforms into a imago, copulates, and lays eggs, it is investigated whether or not the eggs diapause without embryogenesis. If the specimen does not have diapause activity, the laid eggs hatch out to larvae in about 10 days. In case that the specimen has the hormonal activity, the color of the eggs becomes blackish-brown which is not observed in non-diapausing eggs. The embryogenesis is terminated in the colored eggs, which do not hatch out to larvae. The hormonal activity is determined by calculating what percentage of the eggs laid by one imago diapauses. One diapause hormone unit is the amount of the hormone which make 50% of the laid eggs diapause. In this invention, the isolated diapause hormone was 0.1 ng/unit.

4. Synthesis of Diapause Hormone

Two kinds of diapause hormones consisting of the following amino acid sequence, in which the amino acid 19 is Cys (SEQ ID NO: 1) or Trp (SEQ ID NO: 2), are synthesized:

```
         1              5                 10                15
H—Thr—Asp—Met—Lys—Asp—Glu—Ser—Asp—Arg—Gly—Ala—His—Ser—Glu—Arg—Gly—Ala—
```

Leu—X—Phe—Gly—Pro—Arg—Leu—NH$_2$ wherein X is Cys or Trp.

Method

Amino acids protected by protecting groups including t-Boc are condensed by dicyclohexylcarbodiimide on p-methyl-benzhydrylamine resin in order of the above amino acid sequence to obtain a protected crude peptide. The t-Boc groups are removed by trifluoroacetic acid (TFA) and the protecting groups other than t-Boc groups are by hydrogen fluoride (HF) from the protected crude peptide, which is eluted with 60% acetonitrile-water (0.1% TFA) to obtain a crude peptide. The peptide is isolated by use of ODS (Octadecyl silan) column with 0% to 60% acetonitril-water (0.1% TFA) gradient system. In the case of Trp$_{19}$, the formyl group has yet bound at the N-position of Trp. In order to remove the formyl group from the Trp-N-formyl peptide, the peptide is dissolved in 20 mM piperidine solution and reacted until an absorption at 310 nm disappears and shifts to 280 nm.

The resulting peptide is purified by ODS type HPLC to obtain a pure peptide.

Both of these synthesized peptides in which the amino acid 19 is Cys and Trp also have diapause activity like diapause hormone obtained from silkworm pupas.

---

We claim:

1. A protein of the formula:

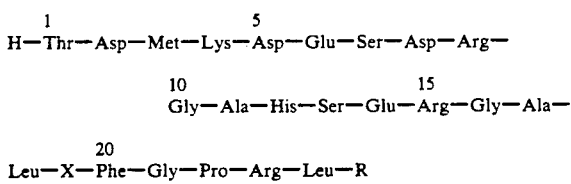

wherein X is Cys or Trp and R is OH or NH$_2$, said protein having a hormonal activity of 0.1 ng/unit, said unit corresponding to the amount of protein which makes 50% of a group of eggs laid by an N$_4$ silkworm line diapause.

2. The protein of claim 1, wherein X is Cys and R is OH.
3. The protein of claim 1, wherein X is Cys and R is NH$_2$.
4. The protein of claim 1, wherein X is Trp.
5. The protein of claim 4, wherein R is OH.
6. An isolated and purified protein consisting essentially of the formula:

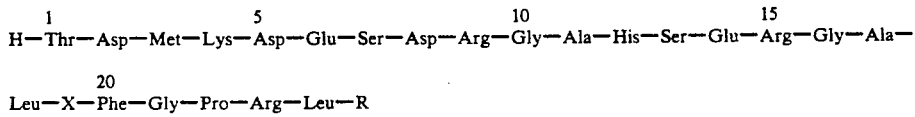

wherein X is Cys or Trp and R is OH or NH$_2$.
7. The protein of claim 6, wherein X is Cys.
8. The protein of claim 7, wherein R is OH.
9. The protein of claim 6, wherein X is Trp.
10. The protein of claim 9, wherein R is OH.

* * * * *